US009820867B2

(12) United States Patent
Tepper et al.

(10) Patent No.: US 9,820,867 B2
(45) Date of Patent: Nov. 21, 2017

(54) THREE COLUMN SPINAL FIXATION IMPLANTS AND ASSOCIATED SURGICAL METHODS

(71) Applicants: Gil Tepper, Beverly Hills, CA (US); James Spitler, Boca Raton, FL (US); Peter Harris, Boca Raton, FL (US)

(72) Inventors: Gil Tepper, Beverly Hills, CA (US); James Spitler, Boca Raton, FL (US); Peter Harris, Boca Raton, FL (US)

( * ) Notice: Subject to any disclaimer, the term of this patent is extended or adjusted under 35 U.S.C. 154(b) by 35 days.

(21) Appl. No.: 15/154,099

(22) Filed: May 13, 2016

(65) Prior Publication Data

US 2017/0119537 A1    May 4, 2017

Related U.S. Application Data

(60) Provisional application No. 62/160,754, filed on May 13, 2015, provisional application No. 62/166,635, (Continued)

(51) Int. Cl.
*A61F 2/44* (2006.01)
*A61F 2/30* (2006.01)
(Continued)

(52) U.S. Cl.
CPC .......... *A61F 2/447* (2013.01); *A61B 17/7032* (2013.01); *A61B 17/7035* (2013.01);
(Continued)

(58) Field of Classification Search
CPC ....... A61F 2/447; A61F 2/44; A61F 2002/448
See application file for complete search history.

(56) References Cited

U.S. PATENT DOCUMENTS

| | | | | |
|---|---|---|---|---|
| 6,090,143 A | * | 7/2000 | Meriwether | A61F 2/446 623/17.11 |
| 6,575,979 B1 | * | 6/2003 | Cragg | A61B 17/1671 606/279 |

(Continued)

*Primary Examiner* — Ellen C Hammond
*Assistant Examiner* — Stuart S Bray
(74) *Attorney, Agent, or Firm* — Clements Bernard Walker PLLC; Christopher L. Bernard

(57) ABSTRACT

A three column spinal fixation implant, including: an anterior cage configured to be disposed in an intervertebral space between adjacent vertebral bodies in a spine of a patient; an anterior plate coupled to the anterior cage; a pair of anterior screws coupled to the anterior cage and the anterior plate and extending posteriorly from the anterior cage and the anterior plate through a portion of one or more of the adjacent vertebral bodies and into or through posterior bony structures of the spine of the patient; a pair of anterior screws coupled to the anterior plate and extending posteriorly from the anterior plate through a portion of one or more of the adjacent vertebral bodies and into or through posterior bony structures of the spine of the patient; a plurality of posterior headbodies coupled to the anterior screws opposite the anterior cage and the anterior plate; and one or more connecting structures coupled to the plurality of posterior headbodies; wherein the three column spinal fixation implant provides structural stability to the spine of the patient across a first anterior column, a second middle column, and a third posterior column thereof.

12 Claims, 26 Drawing Sheets

Related U.S. Application Data filed on May 26, 2015, provisional application No. 62/185,751, filed on Jun. 29, 2015.

(51) Int. Cl.
  *A61B 17/70*     (2006.01)
  *A61B 17/86*     (2006.01)

(52) U.S. Cl.
  CPC ...... *A61B 17/7044* (2013.01); *A61B 17/7059* (2013.01); *A61B 17/8605* (2013.01); *A61B 17/8685* (2013.01); *A61F 2/30771* (2013.01); *A61F 2002/3008* (2013.01); *A61F 2002/30433* (2013.01); *A61F 2002/30828* (2013.01); *A61F 2002/448* (2013.01); *A61F 2310/00023* (2013.01)

(56) References Cited

U.S. PATENT DOCUMENTS

| | | | | |
|---|---|---|---|---|
| 7,674,293 | B2* | 3/2010 | Kuiper | A61B 17/686 623/17.11 |
| 7,871,441 | B2* | 1/2011 | Eckman | A61F 2/4455 623/17.11 |
| 8,206,418 | B2* | 6/2012 | Triplett | A61B 17/7064 606/246 |
| 8,562,649 | B2* | 10/2013 | Triplett | A61B 17/1757 606/247 |
| 8,900,309 | B2* | 12/2014 | James | A61F 2/442 623/17.16 |
| 9,119,732 | B2* | 9/2015 | Schifano | A61F 2/4611 |
| 9,283,084 | B1* | 3/2016 | O'Hara | A61F 2/447 |
| 9,370,433 | B1* | 6/2016 | Morris | A61F 2/4455 |
| 9,402,735 | B2* | 8/2016 | McDonough | A61B 17/1728 |
| 9,622,875 | B2* | 4/2017 | Moskowitz | A61F 2/442 |
| 9,744,049 | B2* | 8/2017 | Kueenzi | A61F 2/4425 |
| 9,744,052 | B2* | 8/2017 | Moskowitz | A61F 2/447 |
| 2007/0016298 | A1* | 1/2007 | Recoules-Arche | A61F 2/4455 623/17.11 |
| 2008/0033440 | A1* | 2/2008 | Moskowitz | A61B 17/0642 606/251 |
| 2008/0177307 | A1* | 7/2008 | Moskowitz | A61B 17/0642 606/246 |
| 2009/0112269 | A1* | 4/2009 | Lieberman | A61B 17/7064 606/301 |
| 2009/0224023 | A1* | 9/2009 | Moskowitz | A61B 17/0642 227/181.1 |
| 2011/0160772 | A1* | 6/2011 | Arcenio | A61B 17/7053 606/248 |
| 2011/0160861 | A1* | 6/2011 | Jimenez | A61F 2/4465 623/17.16 |
| 2012/0029636 | A1* | 2/2012 | Ragab | A61F 2/4425 623/17.11 |
| 2012/0185048 | A1* | 7/2012 | Phelps | A61F 2/4455 623/17.16 |
| 2013/0023992 | A1* | 1/2013 | Moskowitz | A61F 2/447 623/17.16 |
| 2013/0158669 | A1* | 6/2013 | Sungarian | A61F 2/442 623/17.16 |
| 2013/0218276 | A1* | 8/2013 | Fiechter | A61F 2/4455 623/17.16 |
| 2014/0012380 | A1* | 1/2014 | Laurence | A61F 2/4465 623/17.16 |
| 2014/0249629 | A1* | 9/2014 | Moskowitz | A61B 17/0642 623/17.15 |
| 2015/0142115 | A1* | 5/2015 | Richerme | A61F 2/447 623/17.16 |
| 2016/0095632 | A1* | 4/2016 | Faulhaber | A61B 17/7064 623/17.16 |
| 2016/0302941 | A1* | 10/2016 | Reiley | A61F 2/447 |
| 2017/0014239 | A1* | 1/2017 | Seifert | A61F 2/447 |
| 2017/0246007 | A1* | 8/2017 | Chataigner | A61F 2/4455 |

* cited by examiner ent application/patent claims the benefit of
THREE COLUMN SPINAL FIXATION IMPLANTS AND ASSOCIATED SURGICAL METHODS

CROSS-REFERENCE TO RELATED APPLICATIONS

The present patent application/patent claims the benefit of priority of U.S. Provisional Patent Application No. 62/160,754, filed on May 13, 2015, and entitled "THREE COLUMN FIXATED STAND-ALONE SPINAL IMPLANT," U.S. Provisional Patent Application No. 62/166,635, filed on May 26, 2015, and entitled "TARGETING DEVICE AND METHOD FOR THREE COLUMN FIXATED STAND-ALONE SPINAL IMPLANT," and U.S. Provisional Patent Application No. 62/185,751, filed on Jun. 29, 2015, and entitled "THREE COLUMN FIXATION HAVING SCREW COUPLING ABILITY," the contents of all of which are incorporated in full by reference herein.

FIELD OF THE INVENTION

The present invention relates generally to spinal fixation implants and associated surgical methods. More specifically, the present invention relates to three column spinal fixation implants and associated surgical methods operable for simultaneously anteriorly and posteriorly stabilizing a portion of the spine at a given level.

BACKGROUND OF THE INVENTION

It is common in spinal surgery to perform a two incision operation, with implants placed from the front (i.e. anterior) portion of the vertebral column and supplemental fixation placed from the back (i.e. posterior) portion of the vertebral column. This effectively creates fixation in all three columns of the spine, and, hence, superior stabilization. The three columns of the spine—anterior 10, middle 12, and posterior 14—are shown in FIG. 1. To create a stable, solid fusion, a surgeon typically needs to stabilize all three columns in order to prevent micro-motion from occurring, which can lead to non-union of the segment (i.e. pseudoarthrosis).

To accomplish this, the surgeon frequently utilizes two different surgical approaches (anterior and posterior) and two separate spinal systems to achieve a stable construct. This is done using an Anterior Lumbar Interbody Fusion (ALIF) cage, with or without supplemental screws, via the anterior approach, and then using posterior pedicle screws or facet screws from the back of the patient. The surgeon performs an anterior discectomy and places the ALIF cage into the front disc space, and may secure it with screws into the vertebrae. Then the surgeon flips the patient over and places the screws from the back. This posterior approach is time consuming, technically challenging, and, for accuracy, sometimes it is robotically assisted to minimize the risk of nerve injury.

Thus, truly unified three column spinal fixation implants and associated surgical methods operable for simultaneously anteriorly and posteriorly stabilizing a portion of the spine at a given level are still needed in the art.

BRIEF SUMMARY OF THE INVENTION

In various exemplary embodiments, the present invention allows a surgeon to insert one portion of an implant system with anterior screws from the front, and then connect posterior screws to the anterior screws from the back. This can be accomplished using one unified system and 'coupling' portions of the system together from the front and back, thereby creating a true 360 degrees of fixation. In general, it is novel to couple anterior and posterior implant systems to provide three column spinal fixation and stabilizing compression. The present invention provides enhanced operative simplicity and reduced operative time, with superior operative functionality. It is ideally suited for use in the lumbar spine, with the anterior aspect exposed at the operative level. Three column fixation is achieved when the anterior column across the vertebral body is fused and two posterior column fixation points (across the load bearing facet joints) are also fused, such that immobility and stability of the level is achieved, thereby eliminating instability and nerve irritation.

In one exemplary embodiment, a three column spinal fixation implant, comprises: an anterior cage configured to be disposed in an intervertebral space between adjacent vertebral bodies in a spine of a patient; one or more anterior screws coupled to the anterior cage and extending posteriorly from the anterior cage through a portion of one or more of the adjacent vertebral bodies and into or through posterior bony structures of the spine of the patient; one or more posterior headbodies coupled to the one or more anterior screws opposite the anterior cage; and one or more connecting structures coupled to the one or more posterior headbodies; wherein the three column spinal fixation implant provides structural stability to the spine of the patient across a first anterior column, a second middle column, and a third posterior column thereof. The anterior cage comprises one or more friction surfaces configured to hold the anterior cage in the intervertebral space. The anterior cage defines one or more internal voids configured to contain a bone graft material. The anterior cage is manufactured from one or more of a surgically implantable polymeric material and a surgically implantable metallic material. Optionally, the one or more posterior headbodies are coupled to the one or more anterior screws via one or more posterior screws that threadingly engage the one or more anterior screws in a coaxial alignment. Alternatively, the one or more posterior headbodies are coupled to the one or more anterior screws via one or more compression fittings that compressively engage the one or more anterior screws in a coaxial alignment. Optionally, the implant also comprises an anterior plate coupled to the anterior cage. The one or more anterior screws are coupled to the anterior cage through the anterior plate. Optionally, the one or more anterior screws comprise a pair of anterior screws that are coupled to both the anterior cage and the anterior plate and a pair of anterior screws that are coupled only to the anterior plate. Optionally, the one or more connecting structures comprise one or more connecting rods that are coupled to adjacent posterior headbodies. Alternatively, the one or more connecting structures are coupled to adjacent posterior headbodies through a space between adjacent spinous processes of the spine of the patient, thereby distracting the adjacent spinous processes. Alternatively, the one or more connecting structures are coupled to adjacent posterior headbodies parallel to adjacent spinous processes of the spine of the patient, thereby distracting the adjacent spinous processes. Alternatively, the one or more connecting structures couple the one or more headbodies to one or more facets of the spine of the patient.

In another exemplary embodiment, a three column spinal fixation implant, comprises: an anterior cage configured to be disposed in an intervertebral space between adjacent vertebral bodies in a spine of a patient; an anterior plate coupled to the anterior cage; a pair of anterior screws coupled to the anterior cage and the anterior plate and extending posteriorly from the anterior cage and the anterior plate through a portion of one or more of the adjacent vertebral bodies and into or through posterior bony structures of the spine of the patient; a pair of anterior screws coupled to the anterior plate and extending posteriorly from the anterior plate through a portion of one or more of the adjacent vertebral bodies and into or through posterior bony structures of the spine of the patient; a plurality of posterior headbodies coupled to the anterior screws opposite the anterior cage and the anterior plate; and one or more connecting structures coupled to the plurality of posterior headbodies; wherein the three column spinal fixation implant provides structural stability to the spine of the patient across a first anterior column, a second middle column, and a third posterior column thereof.

In a further exemplary embodiment, a three column spinal fixation method, comprises: disposing an anterior cage in an intervertebral space between adjacent vertebral bodies in a spine of a patient; providing one or more anterior screws coupled to the anterior cage and extending posteriorly from the anterior cage through a portion of one or more of the adjacent vertebral bodies and into or through posterior bony structures of the spine of the patient; coupling one or more posterior headbodies to the one or more anterior screws opposite the anterior cage; and coupling one or more connecting structures to the one or more posterior headbodies; wherein the three column spinal fixation method provides structural stability to the spine of the patient across a first anterior column, a second middle column, and a third posterior column thereof. The anterior cage comprises one or more friction surfaces configured to hold the anterior cage in the intervertebral space. The anterior cage defines one or more internal voids configured to contain a bone graft material. The anterior cage is manufactured from one or more of a surgically implantable polymeric material and a surgically implantable metallic material. Optionally, the one or more posterior headbodies are coupled to the one or more anterior screws via one or more posterior screws that threadingly engage the one or more anterior screws in a coaxial alignment. Alternatively, the one or more posterior headbodies are coupled to the one or more anterior screws via one or more compression fittings that compressively engage the one or more anterior screws in a coaxial alignment. Optionally, the method also comprises providing an anterior plate coupled to the anterior cage. The one or more anterior screws are coupled to the anterior cage through the anterior plate. Optionally, the one or more anterior screws comprise a pair of anterior screws that are coupled to both the anterior cage and the anterior plate and a pair of anterior screws that are coupled only to the anterior plate. Optionally, the one or more connecting structures comprise one or more connecting rods that are coupled to adjacent posterior headbodies. Alternatively, the one or more connecting structures are coupled to adjacent posterior headbodies through a space between adjacent spinous processes of the spine of the patient, thereby distracting the adjacent spinous processes. Alternatively, the one or more connecting structures are coupled to adjacent posterior headbodies parallel to adjacent spinous processes of the spine of the patient, thereby distracting the adjacent spinous processes. Alternatively, the one or more connecting structures couple the one or more headbodies to one or more facets of the spine of the patient.

BRIEF DESCRIPTION OF THE DRAWINGS

The present invention is illustrated and described herein with reference to the various drawings, in which like reference numbers are used to denote like device components/method steps, and in which.

DETAILED DESCRIPTION OF THE INVENTION

Again, in various exemplary embodiments, the present invention allows a surgeon to insert one portion of an implant system with anterior screws from the front, and then connect posterior screws to the anterior screws from the back. This can be accomplished using one unified system and 'coupling' portions of the system together from the front and back, thereby creating a true 360 degrees of fixation. In general, it is novel to couple anterior and posterior implant systems to provide three column spinal fixation and stabilizing compression. The present invention provides enhanced operative simplicity and reduced operative time, with superior operative functionality.

Figure 1:
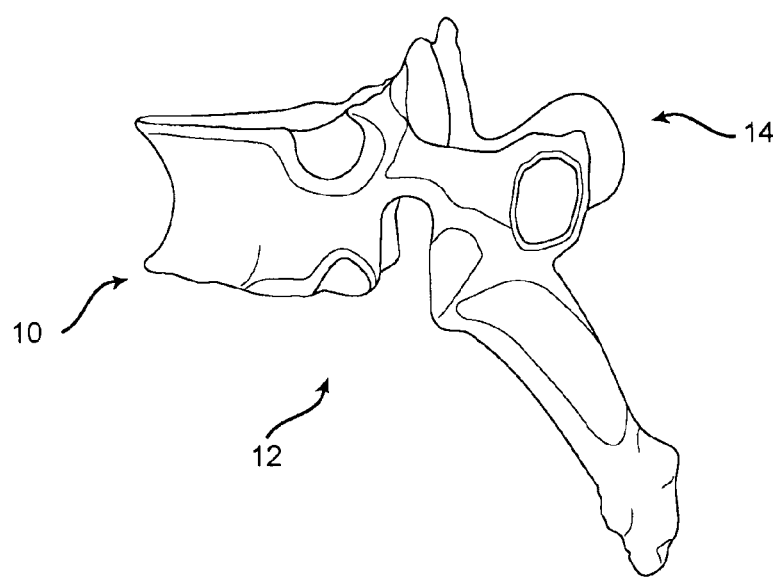
FIG. 1 is a perspective view of a portion of the spine, highlighting the three columns—the anterior column, the middle column, and the posterior column.
Figure 2:
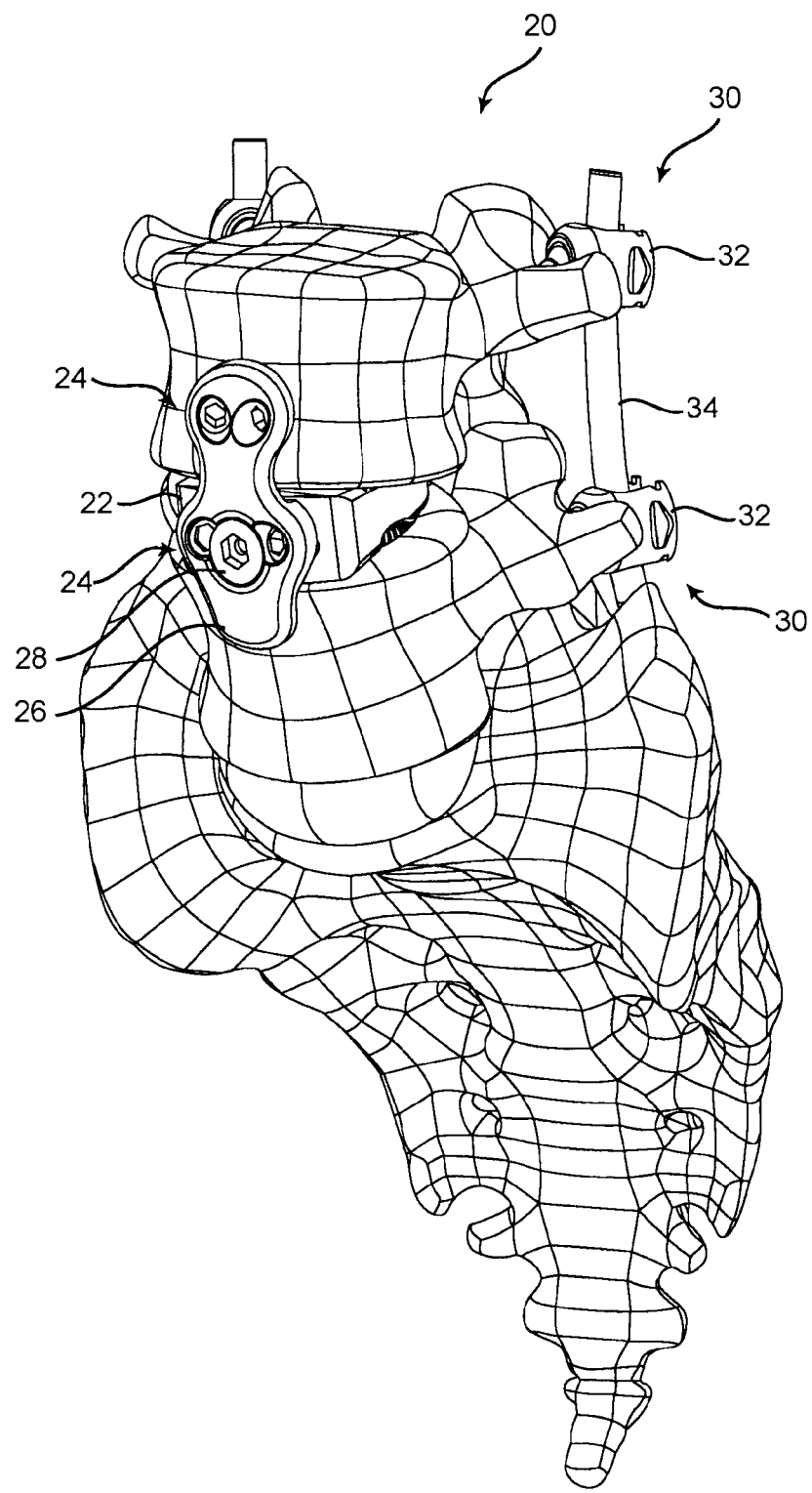
FIG. 2 is a perspective view of one exemplary embodiment of the three column spinal fixation implant of the present invention in an installed configuration, highlighting the use of an optional anterior plate.
Figure 3:
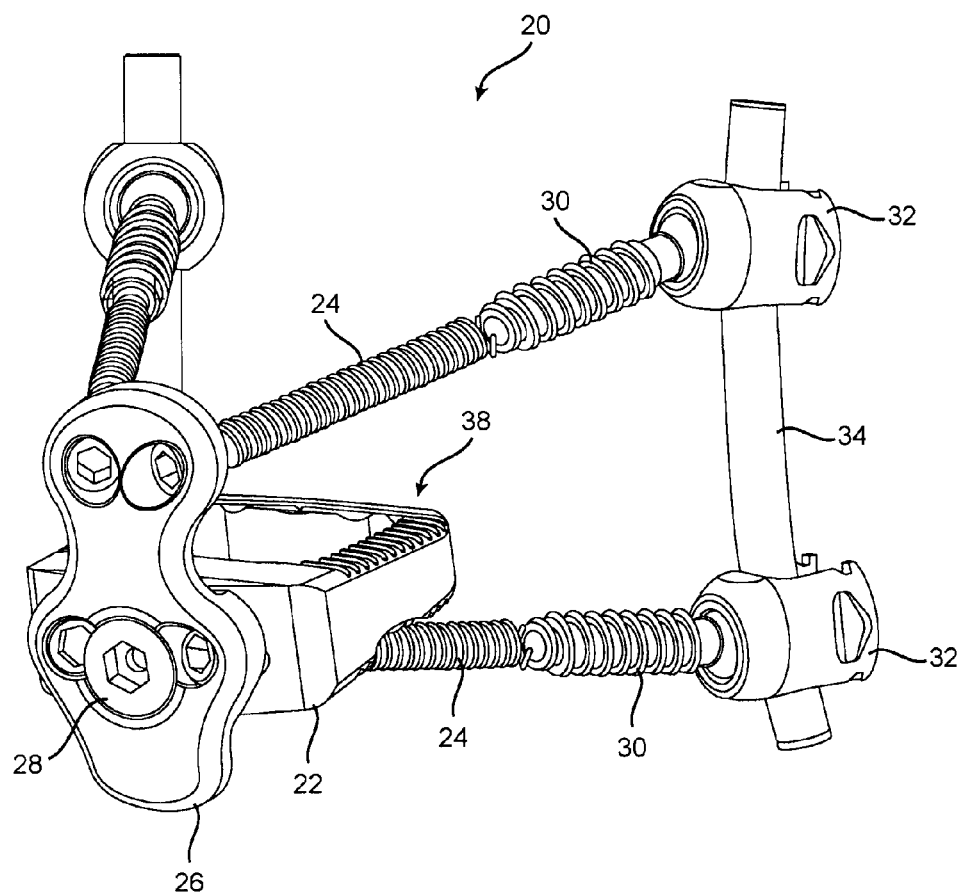
FIG. 3 is a perspective view of one exemplary embodiment of the three column spinal fixation implant of the present invention in an assembled configuration, again highlighting the use of an optional anterior plate.
Figure 4:
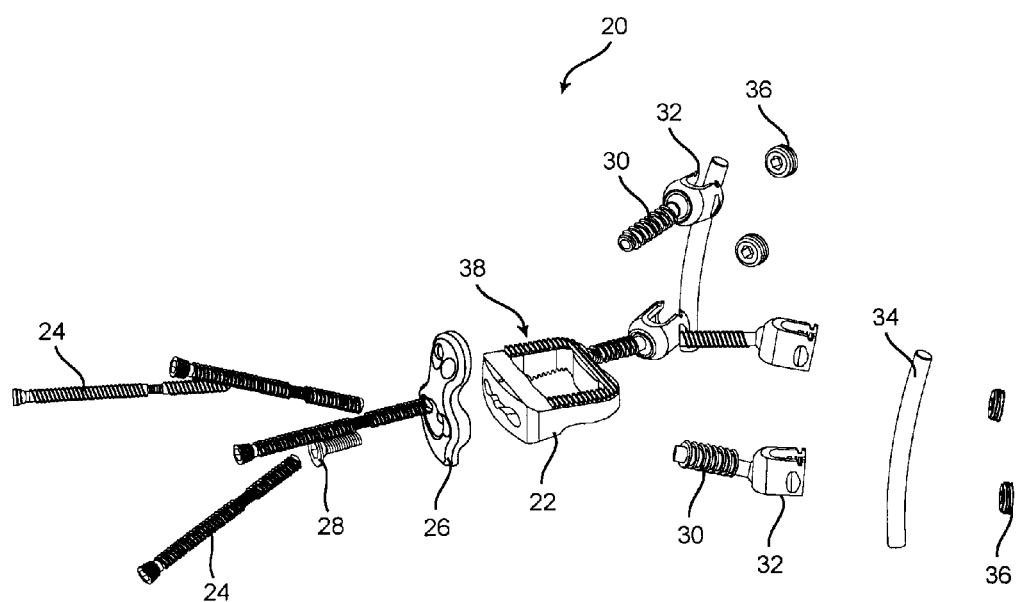
FIG. 4 is a perspective view of one exemplary embodiment of the three column spinal fixation implant of the present invention in an exploded configuration, again highlighting the use of an optional anterior plate.

Referring now specifically to FIGS. 2-4, in one exemplary embodiment, the spinal implant 20 of the present invention includes an anterior cage 22 in the form of an interbody spacer that is disposed in the disc space of a desired segment. A plurality of anterior screws 24 are threaded through the anterior cage 22 into the adjacent vertebrae, thereby preventing the anterior cage 22 from moving and migrating in the disc space while maintaining a desired degree of distraction of the articulating surfaces and providing a void for bony ingrowth and fusion, for example. Accordingly, the anterior cage 22 may include a plurality of friction surfaces 38 (FIGS. 3 and 4) on the lower and/or upper surfaces thereof, and may be made of a polymer material, such as polyetheretherketone (PEEK), titanium, or some other biocompatible material. In one exemplary embodiment, a pair of anterior screws 24 (for example) are threaded through the anterior cage 22 into the adjacent lower vertebra, while a pair of anterior screws 24 (for example) are threaded through the anterior cage 22 into the adjacent upper vertebra. These anterior screws 24 can be locked into place and prevented from backing out via an appropriate locking plate, locking mechanism, or locking screw disposed over the head(s) of the anterior screws 24. In another exemplary embodiment, an anterior plate 26 is secured to the anterior cage 22 via a coupling bolt 28 and a pair of anterior screws 24 (for example) are threaded through the anterior cage 22, either through or beneath the anterior plate 26, into the adjacent lower vertebra. A pair of anterior screws 24 (for example) are then threaded through the anterior plate 26 into the adjacent upper vertebra. Again, these anterior screws 24 can be locked into place and prevented from backing out via an appropriate locking plate, locking mechanism, or locking screw, which may or may not consist of the anterior plate 26 and/or the coupling bolt 28, disposed over the head(s) of the anterior screws 24. Each of these components is described in greater detail herein below. It will be readily apparent to those of ordinary skill in the art that any number of anterior screws 24 can be used, in any configuration, and at any angle. Some or all of the anterior screws 24 can pass through the anterior cage 22 and/or anterior plate 26, provided the anterior cage 22 is ultimately secured in the disc space and the anterior screws point towards the pedicles or facets of the vertebrae involved. The anterior screws 24 are long enough that they pass through the main vertebral body (i.e. anterior column 10 (FIG. 1)), middle column 12 (FIG. 1), and go through the corresponding pedicle to the edge of the posterior column 14 (FIG. 1) using a fluoroscopically guided targeting device, for example. On the posterior side, a coupling mechanism consisting of posterior screws 30, connected articulating headbodies 32, coupled rods 34, and compressive set screws 36 (FIG. 4) connect the pairs of screws 24 and 30 at the back of the patient. The posterior screws 30 may be coaxially aligned and engaged with the anterior screws 24, or the articulating headbodies 32 can be connected directly to the anterior screws 24 via various mechanisms. This creates a strong unified implant construct that extends across all three vertebral columns with solid fixation and coronal compression. Again, each of these components is described in greater detail herein below.

Procedurally, the surgeon utilizes an anterior approach through the retroperitoneal space of the patient and removes the disc in the regular fashion. He or she then sizes the space for the optimal cage fit with a fluoroscopically guided targeting method, as is described in greater detail herein below. He or she then places the new cage 22 into the disc space attached to the targeting device, for example. This new cage 22 includes a drill guide or the like that connects to the face of the new cage 22 that allows the surgeon to accurately drill the holes into the vertebrae. Alternatively, the anterior plate 26 acts as the drill guide. Using the targeting device, a hole is drilled through the vertebra and into the pedicle at each level. Guide wires may be used initially to help with the trajectory and image guidance. The anterior screws 24 are then placed through the new cage 22 and screwed into the posterior pedicles. The anterior screws 24 are then locked to the front face of the new cage. The wound is closed and the patient is flipped over and an incision at the affected levels is performed at the back. With the pedicle markers in place, exposure and posterior fixation is through a smaller, less invasive approach that is safer and more efficient. The pedicles are exposed and a reamer type of instrument is used to remove bony material around the end of the anterior screws 24. Once the ends of the anterior screws 24 have been cleared, a posterior screw 30 and headbody 32 is coupled to the end of each anterior screw 24, for example. A rod 34 or other coupling device is coupled to pairs of anterior screws 24/posterior screws 30 and locked into position using set screws 36, for example. If desired, a compressor may be used to create additional compression on the implant 20 and adjust the lordosis of the patient. Bone graft material may be placed inside the anterior cage 22 and around the posterior elements.

Since there are relatively large variations in the human anatomy, it may not be possible to get the required angle of the screw projection into the pedicles. The incoming screw angle going into the pedicle may be too steep and could cause a screw to break through the edge of the pedicle, causing nerve damage. By having a metal marker or the like on the posterior aspect of the anterior cage 22 and using the targeting device described in greater detail herein below, the anterior cage 22 is placed at such safe depth that allows optimal alignment with the pedicle inlet. Again, if needed in order to get a shallower angle, the anterior plate 26 may be added to the anterior cage 22. The screw holes are offset on the anterior plate 26, allowing the surgeon to target the pedicles and drive the anterior screw 24 from the front of the anterior cage 22 all the way through the pedicle, without breaching the pedicle side wall.

Figure 5:
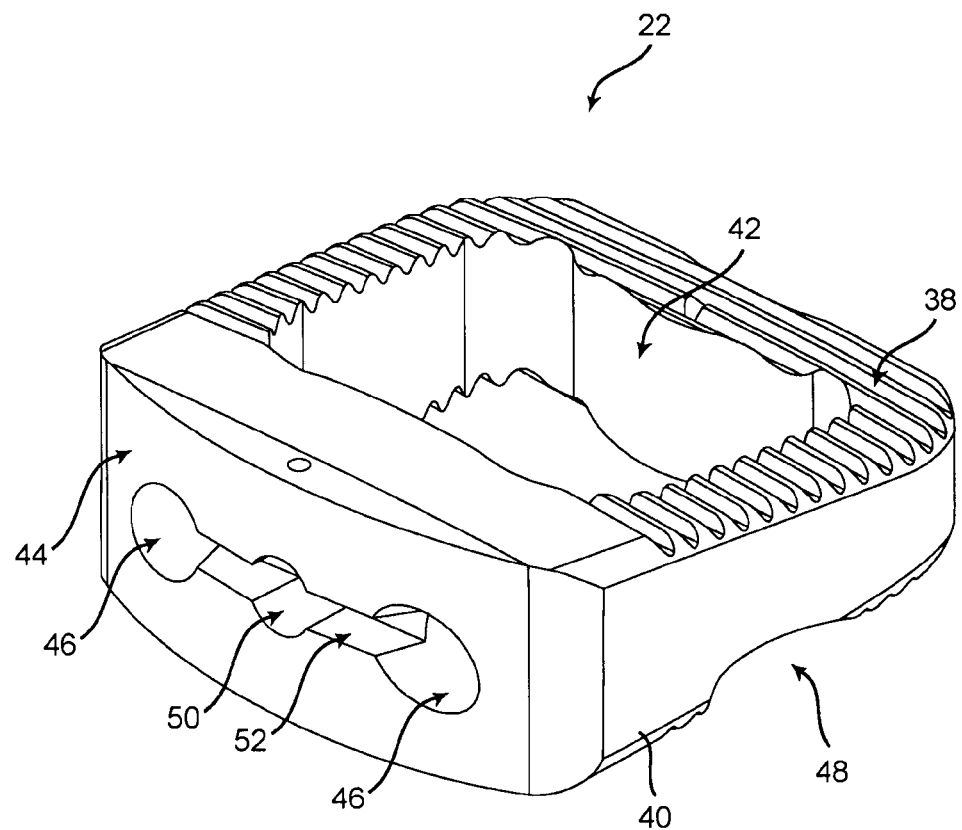
FIG. 5 is a perspective view of one exemplary embodiment of the anterior cage of the three column spinal fixation implant of the present invention.
Figure 6:
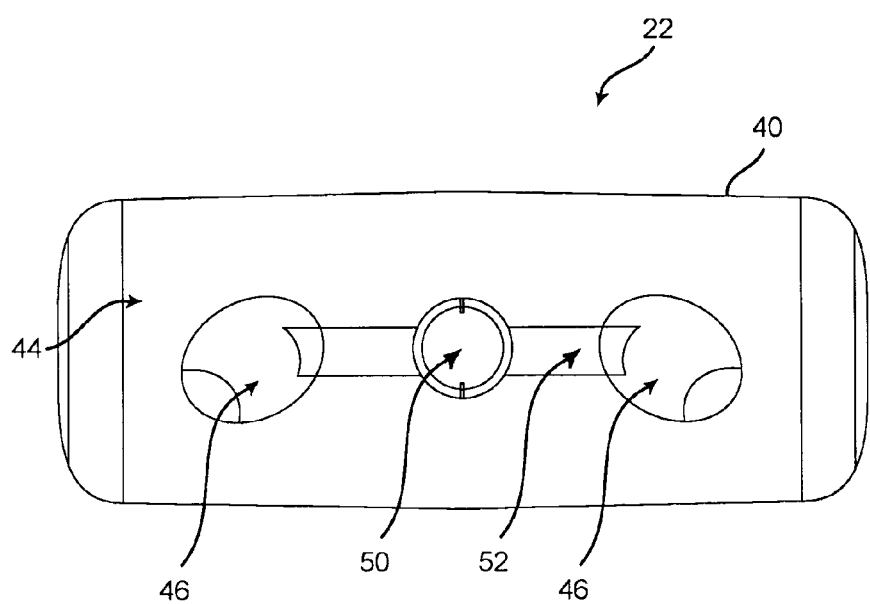
FIG. 6 is a planar end view of one exemplary embodiment of the anterior cage of the three column spinal fixation implant of the present invention.

Referring now specifically to FIGS. 5 and 6, in one exemplary embodiment, the anterior cage 22 consists of a prismatic interbody spacer that is disposed in the disc space of a desired segment. The anterior cage 22 may be made of a polymer material, such as PEEK, titanium, or some other biocompatible material and may include one or more metallic portions for visualization and imaging. The anterior cage 22 may be sized to accommodate a variety of anatomies and provide multiple degrees of vertebral distraction. The anterior cage 22 may include a plurality of friction surfaces 38 (FIG. 5) on the lower and/or upper surfaces configured to prevent the anterior cage 22 from moving and migrating in the disc space while maintaining the desired degree of distraction of the articulating surfaces. Preferably, the body 40 of the anterior cage 22 defines one or more voids 42 for receiving bone graft material for promoting bony ingrowth and fusion. The face 44 and body 40 of the anterior cage 22 include one or more apertures 46 for receiving the anterior screws 24 (FIGS. 2-4). These apertures 46 may be disposed at various downwards/upwards angles to properly orient and direct the anterior screws 24 towards the pedicles at the posterior of the spine. The body 40 may also include appropriate cutaways 48 for this purpose. In the exemplary embodiment illustrated, only downwards oriented anterior screws 24 are disposed through the anterior cage 22 (with upwards oriented anterior screws 24 disposed only through the coupled anterior plate 26 (FIGS. 2-4)). The face 44 and body 40 of the anterior cage 22 further include an aperture 50 for receiving the coupling screw 28 (FIGS. 2-4) associated with the anterior plate 26. Again, this coupling screw 28 and/or the anterior plate 26 may be used as a locking mechanism to hold any of the anterior screws 24 in place and prevent them from backing out. Finally, the face 44 of the anterior cage 22 may include a groove or recess 52 configured to receive a corresponding protruding structure 54 (FIG. 8) on the back surface of the anterior plate 26, thereby ensuring proper alignment of the anterior plate 26 with the anterior cage 22 (see FIG. 9). It should further be noted that the body 40 of the anterior cage 22 may have a wedge shape or tapered leading edge to aide in the insertion of the anterior cage 22 into the disc space.

Figure 7:
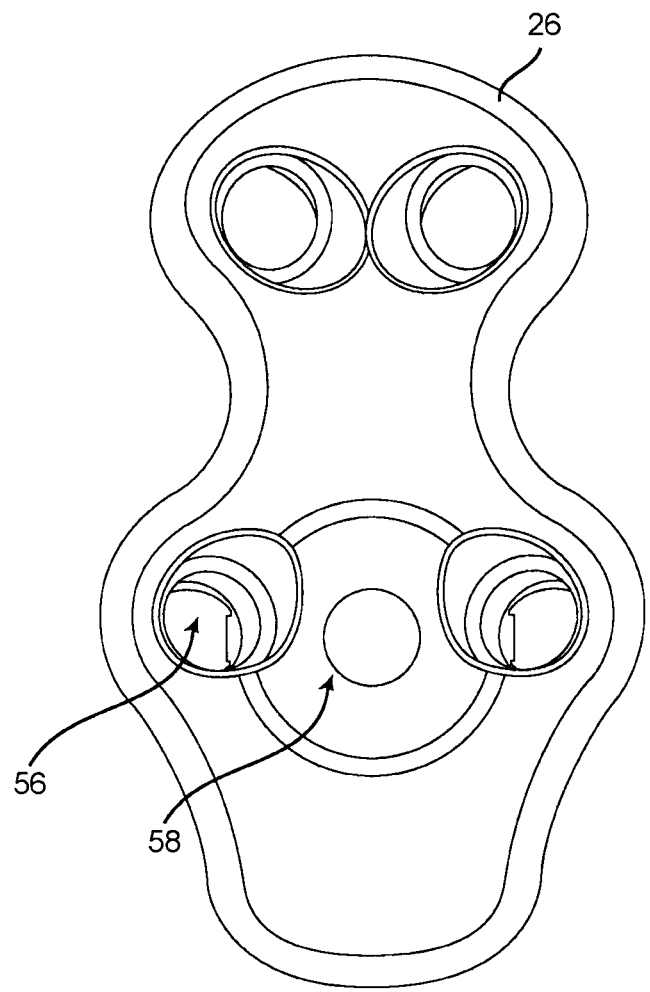
FIG. 7 is a planar view of one exemplary embodiment of the optional anterior plate of the three column spinal fixation implant of the present invention.
Figure 8:
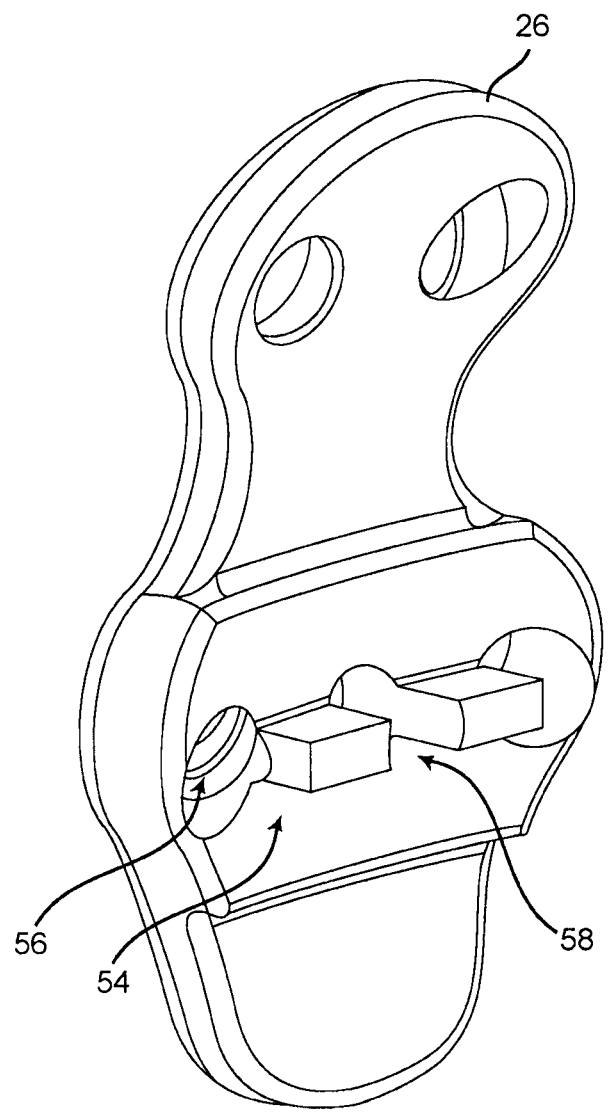
FIG. 8 is rear perspective view of one exemplary embodiment of the optional anterior plate of the three column spinal fixation implant of the present invention.
Figure 9:
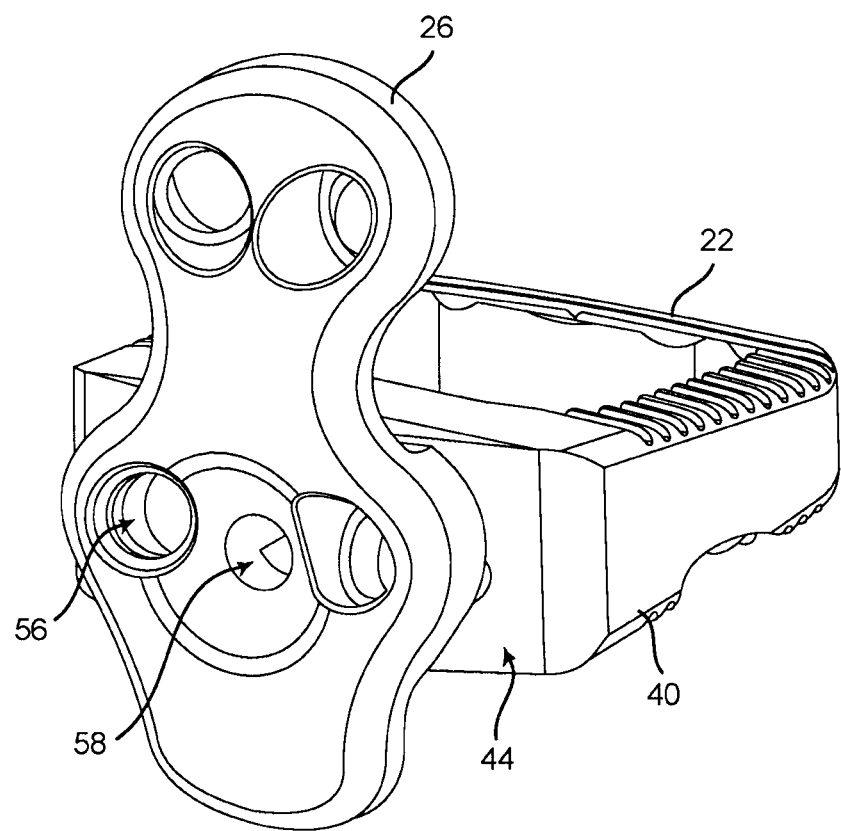
FIG. 9 is a perspective view of one exemplary embodiment of the optional anterior plate of the three column spinal fixation implant of the present invention coupled to the anterior cage of the three column spinal fixation implant of the present invention.

Referring now specifically to FIGS. 7-9, in one exemplary embodiment, the anterior plate 26 consists of a substantially planar structure having curved surfaces that conform to the bony anatomy of the anterior column 10 (FIG. 1) of the lumbar spine, for example. The anterior plate 26 includes one or more apertures 56 for receiving the anterior screws 24 (FIGS. 2-4). These apertures 56 may be disposed at various downwards/upwards angles to properly orient and direct the anterior screws 24 towards the pedicles at the posterior of the spine and may substantially coincide with any number of apertures 46 (FIGS. 5 and 6) of the anterior cage 22 (FIG. 9). Again, in the exemplary embodiment illustrated, only downwards oriented anterior screws 24 are disposed through the anterior cage 22 (with upwards oriented anterior screws 24 disposed only through the coupled anterior plate 26). The anterior plate 26 further includes an aperture 58 for receiving the coupling screw 28 (FIGS. 2-4) associated with the anterior cage 22. Again, this coupling screw 28 and/or the anterior plate 26 may be used as a locking mechanism to hold any of the anterior screws 24 in place and prevent them from backing out. Finally, the back surface of the anterior plate 26 may include a protruding structure 54 (FIG. 8) configured to engage the groove or recess 52 (FIGS. 5 and 6) of the face 44 (FIGS. 5 and 6) of the anterior cage 22, thereby ensuring proper alignment of the anterior plate 26 with the anterior cage 22 (see FIG. 9).

Figure 10:
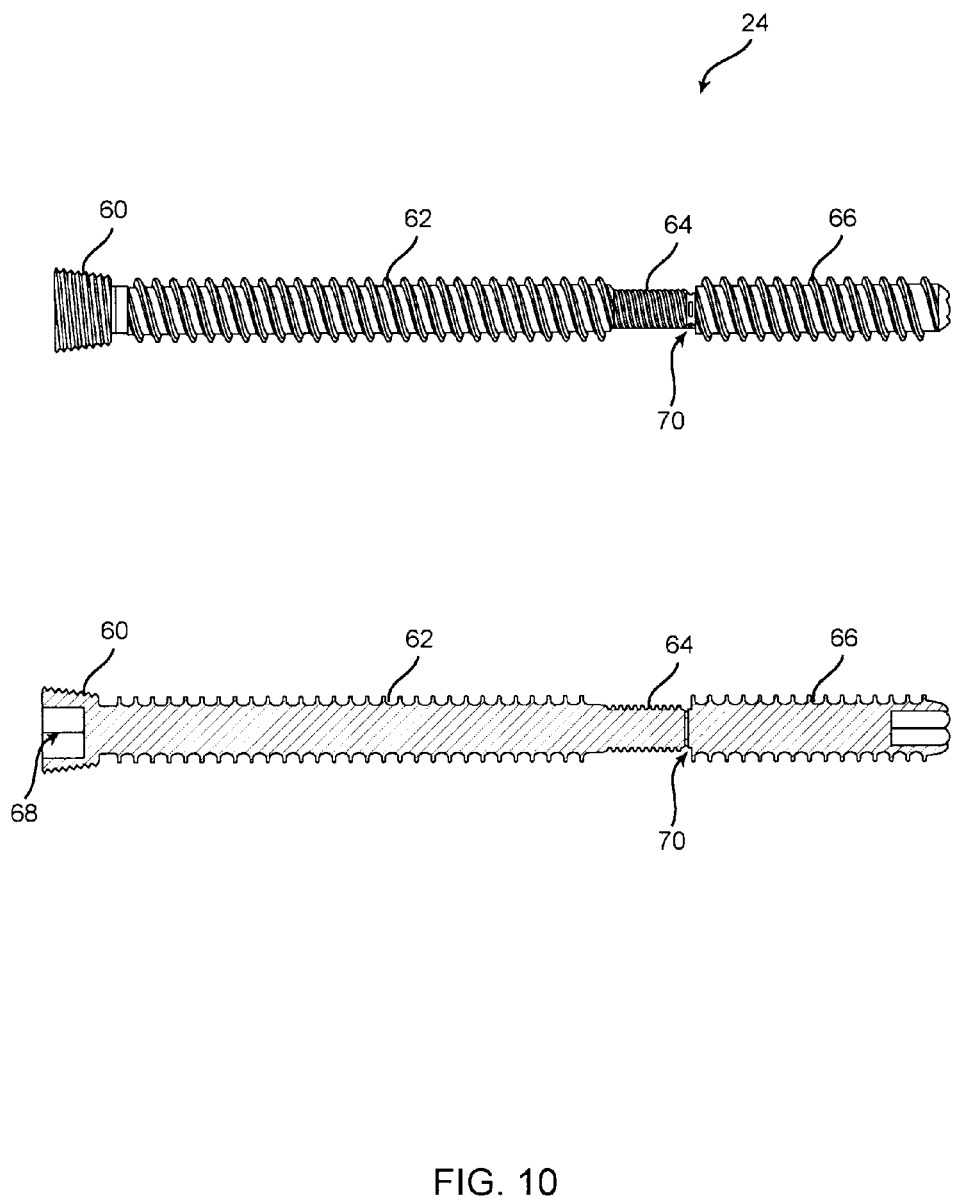
FIG. 10 is a planar and cross-sectional view of one exemplary embodiment of the anterior screw of the three column spinal fixation implant of the present invention.
Figure 11:
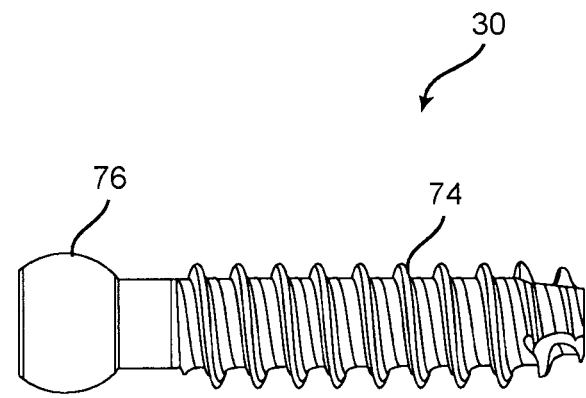
FIG. 11 is a planar and cross-sectional view of one exemplary embodiment of the posterior screw of the three column spinal fixation implant of the present invention.
Figure 11:
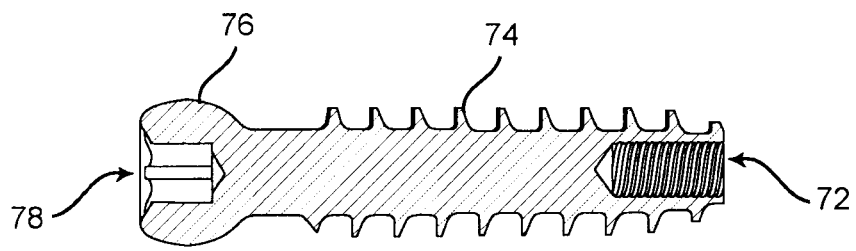
Figure 12:
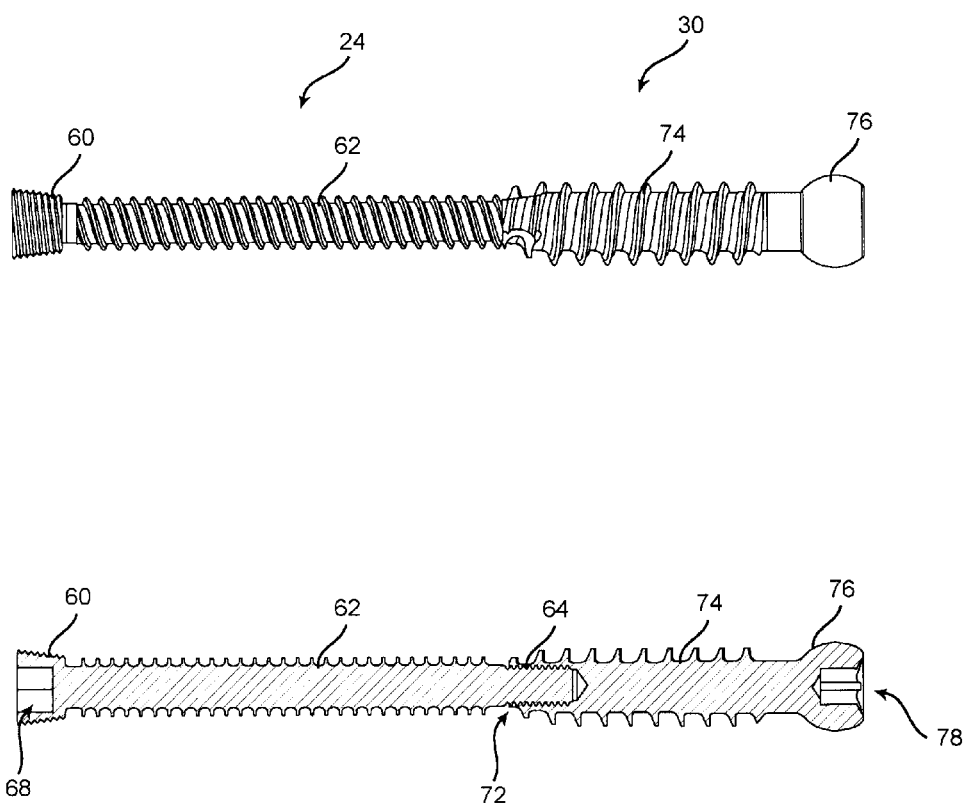
FIG. 12 is a planar and cross-sectional view of one exemplary embodiment of the anterior screw of the three column spinal fixation implant of the present invention coupled to the posterior screw of the three column spinal fixation implant of the present invention.

Referring now specifically to FIGS. 10-12, in one exemplary embodiment, the anterior screw 24 (FIGS. 10 and 12) includes a head portion 60, a threaded shaft portion 62, a threaded posterior engagement portion 64, and a threaded tip portion 66. The head portion 60 includes a recess 68 for receiving a driver or the like and is optionally externally threaded, such that the head portion 60 lockingly engages the corresponding aperture 56 (FIGS. 7-9) of the anterior plate 26 (FIGS. 7-9), for example. The threaded shaft portion 62 engages the corresponding aperture 46 (FIGS. 5 and 6) of the anterior cage 22 (FIGS. 5 and 6), for example, as well as the corresponding bony vertebral structure. The threaded tip portion 66 passes through the corresponding bony vertebral structure and protrudes from the posterior anatomy. The anterior screw 24 includes a narrowed and/or weakened portion 70 just below the threaded tip portion 66, such that, in this exemplary embodiment, the threaded tip portion 66 can be removed from the anterior screw 24, leaving the threaded posterior engagement portion 64 exposed for subsequent coaxial engagement by a corresponding internally threaded chamber 72 of the threaded shaft 74 of the pedicle screw 30 (FIGS. 11 and 12). The pedicle screw 30 also includes a head portion 76 including a recess 78 for receiving a driver or the like. FIG. 12 shows the coaxially assembled anterior screw 24 and posterior screw 30. It should be noted that the pitch of the thread of the pedicle screw 30 preferably matches the pitch of the thread of the end portion of the anterior screw 24 (which may be quad-lead, for example), such that the pedicle screw 30 may be smoothly driven into the posterior bony structure and onto the end portion of the anterior screw 24.

Figure 13:
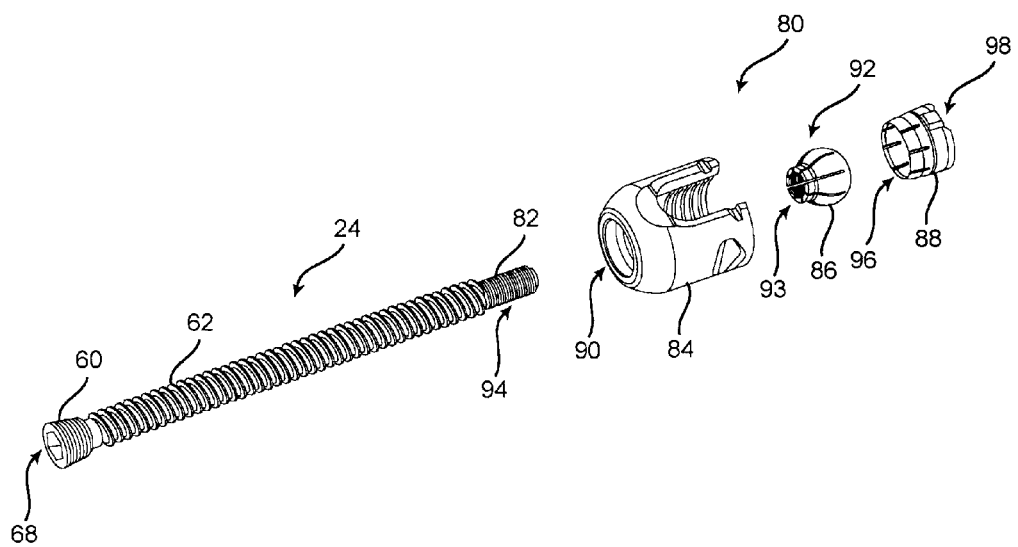
FIG. 13 is an exploded perspective view of another exemplary embodiment of the anterior screw of the three column spinal fixation implant of the present invention, utilizing an integrated headbody.
Figure 14:
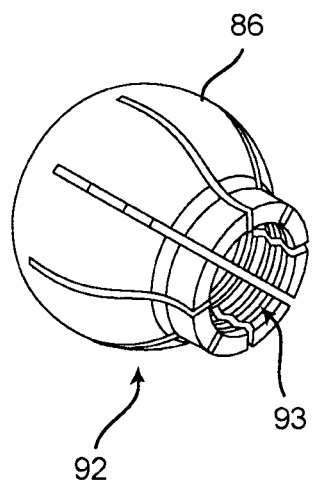
FIG. 14 is a partial perspective view of another exemplary embodiment of the anterior screw of the three column spinal fixation implant of the present invention, highlighting the spherical posterior head member.
Figure 15:
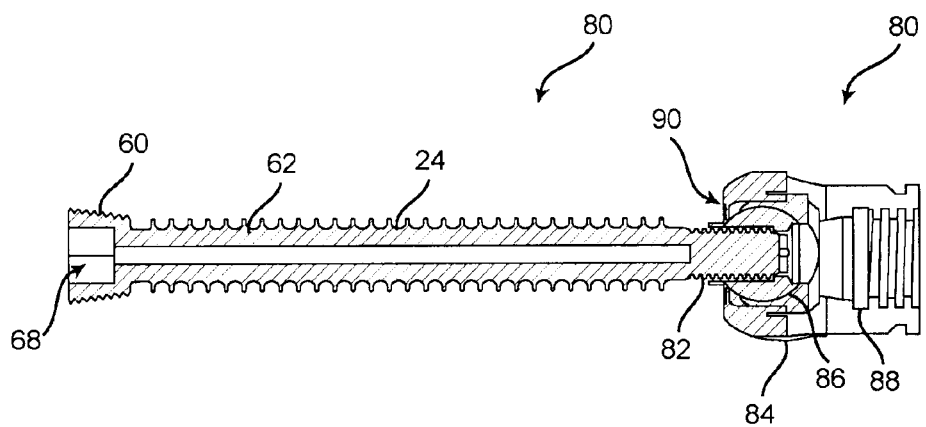
FIG. 15 is a cross-sectional side view of another exemplary embodiment of the anterior screw of the three column spinal fixation implant of the present invention, utilizing an integrated headbody.

Referring now specifically to FIGS. 13-15, in another exemplary embodiment, the anterior screw 24 (FIGS. 13 and 15) includes a head portion 60, a threaded shaft portion 62, a posterior engagement portion 82, and, optionally, a threaded tip portion (not illustrated). The head portion 60 includes a recess 68 for receiving a driver or the like and is optionally externally threaded, such that the head portion 60 lockingly engages the corresponding aperture 56 (FIGS. 7-9) of the anterior plate 26 (FIGS. 7-9), for example. The threaded shaft portion 62 engages the corresponding aperture 46 (FIGS. 5 and 6) of the anterior cage 22 (FIGS. 5 and 6), for example, as well as the corresponding bony vertebral structure. The threaded tip portion, when used, passes through the corresponding bony vertebral structure and protrudes from the posterior anatomy. Optionally, the anterior screw 24 includes a narrowed and/or weakened portion (not illustrated) just below the threaded tip portion, such that, in this exemplary embodiment, the threaded tip portion can be removed from the anterior screw 24, leaving the posterior engagement portion 82 exposed for subsequent coaxial engagement by a corresponding headbody assembly 80. The headbody assembly 80 includes a headbody 84 including an aperture 90. A spherical structure 86 including a plurality of deflection petals 92 (including one or more concentric internal recesses 93) is disposed partially through the aperture 90, where the plurality of deflection petals 92 engage one or more concentric external rings 94 disposed about the posterior engagement portion 82 of the anterior screw 24. In general, the deflection petals 92 are segmented and have a degree of flexibility such that they may be deflected outwards to accommodate the one or more concentric external rings 94 disposed about the posterior engagement portion 82 of the anterior screw 24 and then compress inwards about the one or more concentric external rings 94 disposed about the posterior engagement portion 82 of the anterior screw 24. A saddle structure 88 also including a plurality of deflection petals 96 is disposed concentrically within the headbody 84 adjacent to and partially about the spherical structure 86. Again, in general, the deflection petals 96 are segmented and have a degree of flexibility such that they may be deflected outwards to accommodate the spherical structure 86. The saddle structure 88 also includes a recess for receiving the rod construct. When the rod construct is biased into the headbody 84 by the set screw construct, the saddle structure 88 is biased into and compresses the spherical structure 86, which is based into and compresses the posterior engagement structure 82 of the anterior screw 24. This locks the polyaxial headbody 84 to the anterior screw 24, thereby forming a rigid posterior construct. Preferably, the tip of the posterior engagement structure 82 of the anterior screw 24 can be "clipped" as desired by the surgeon, such that a predetermined degree of protrusion is provided. If the screw is exposed and extending out of the pedicle too far, then one can slide down a cylindrical screw cutter in which a pair of holes intersect to cut/shear the screw between the grooves.

Figure 16:
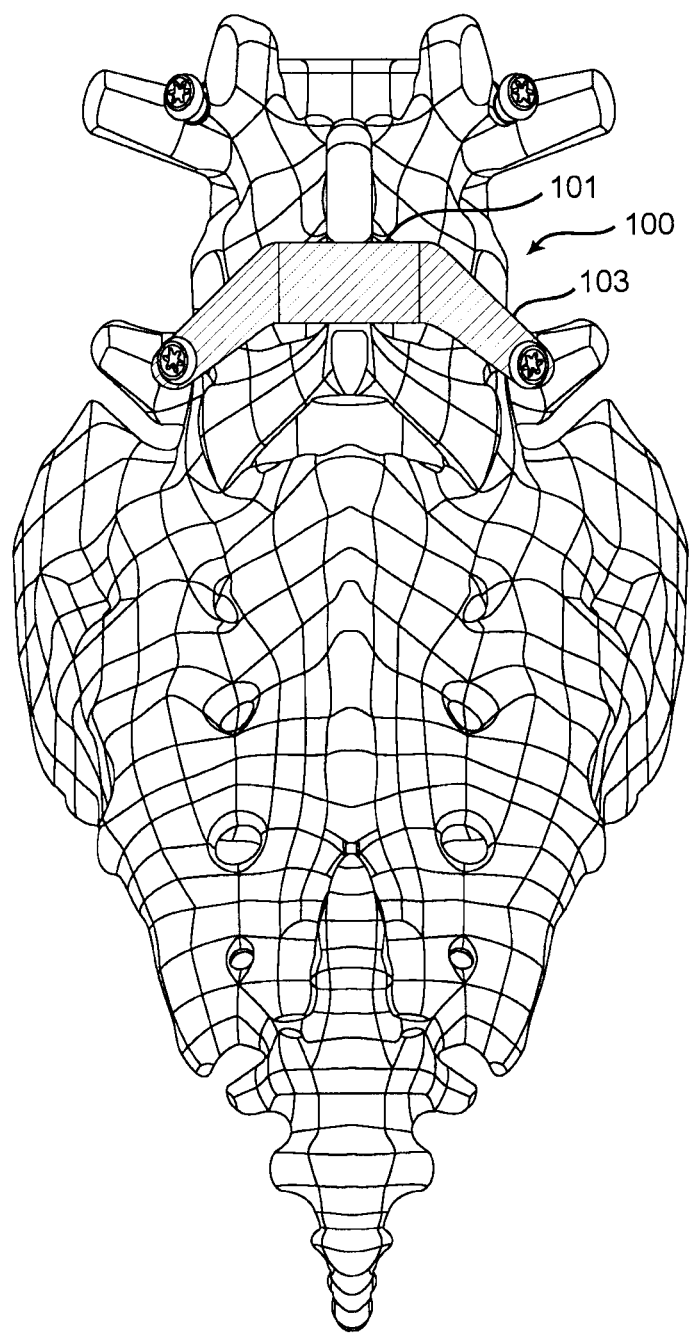
FIG. 16 is a planar view of one exemplary embodiment of an interspinous process distraction device that is coupled to laterally opposed pedicle screws of the three column spinal fixation implant of the present invention, providing slight flexion of the spine at the given level.

FIG. 16 is a planar view of one exemplary embodiment of an interspinous process distraction device 100 that is coupled to laterally opposed pedicle screws of the three column spinal fixation implant of the present invention, providing slight flexion of the spine at the given level. The interspinous process distraction device 100 includes a horizontal spanning member 101 that extends from pedicle screw to pedicle screw between adjacent spinous processes and a pair of opposed pedicle screw engaging members 103 that are optionally disposed at an angle to the horizontal spanning member 101.

Figure 17:
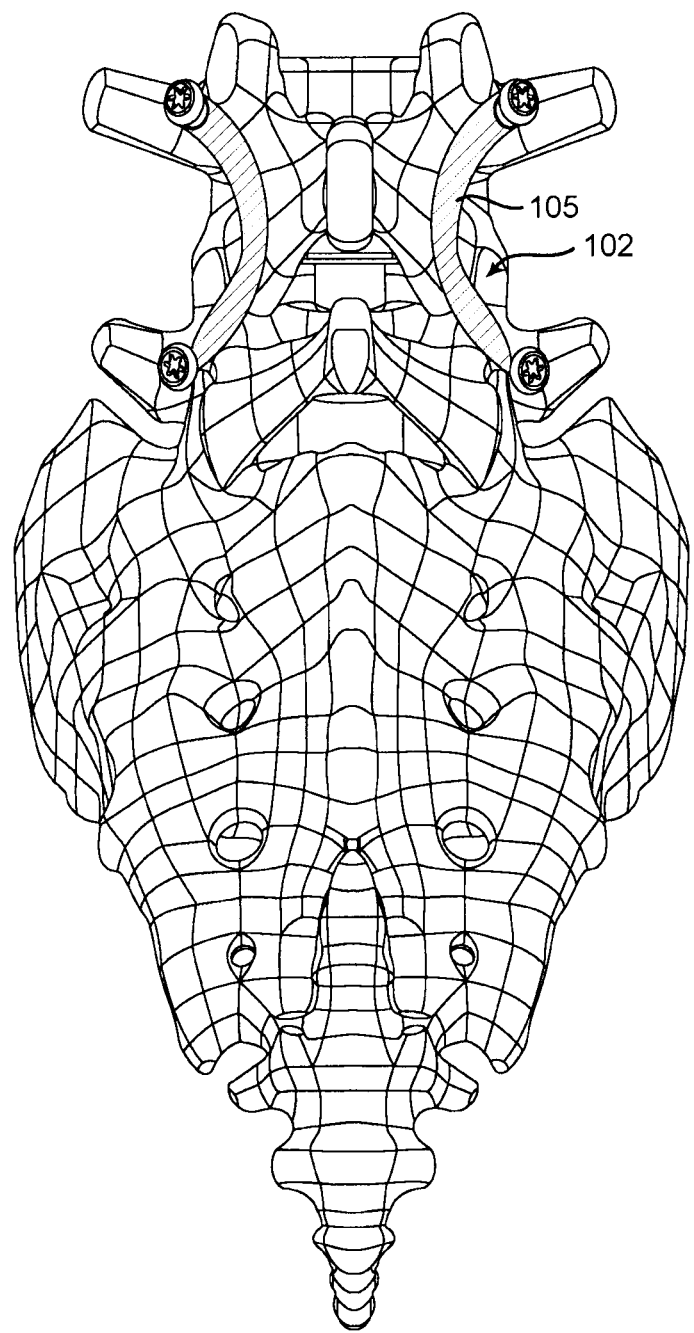
FIG. 17 is a planar view of another exemplary embodiment of an interspinous process distraction device that is coupled to vertically opposed pedicle screws of the three column spinal fixation implant of the present invention, again providing slight flexion of the spine at the given level.

FIG. 17 is a planar view of another exemplary embodiment of an interspinous process distraction device 102 that is coupled to vertically opposed pedicle screws of the three column spinal fixation implant of the present invention, again providing slight flexion of the spine at the given level. The interspinous process distraction device 102 includes a curved spanning member 105 and an integrally formed pair of opposed pedicle screw engaging members.

Figure 18:
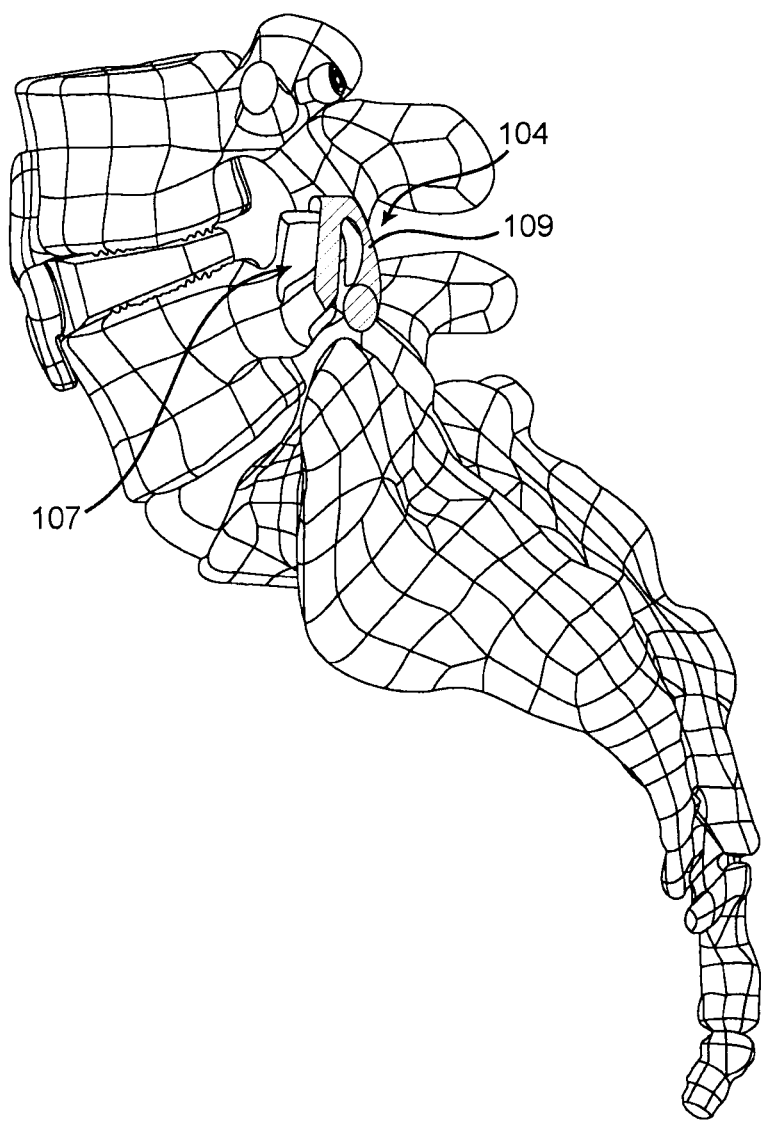
FIG. 18 is a planar view of one exemplary embodiment of a facet attachment device that is coupled to a pedicle screw of the three column spinal fixation implant of the present invention.

FIG. 18 is a planar view of one exemplary embodiment of a facet attachment device 104 that is coupled to a pedicle screw of the three column spinal fixation implant of the present invention. This facet attachment device 104 takes the form of a clip structure 107 that both engages the facet and is secured to the pedicle screw via a suitable appendage 109 extending from the clip structure 107.

Figure 19:
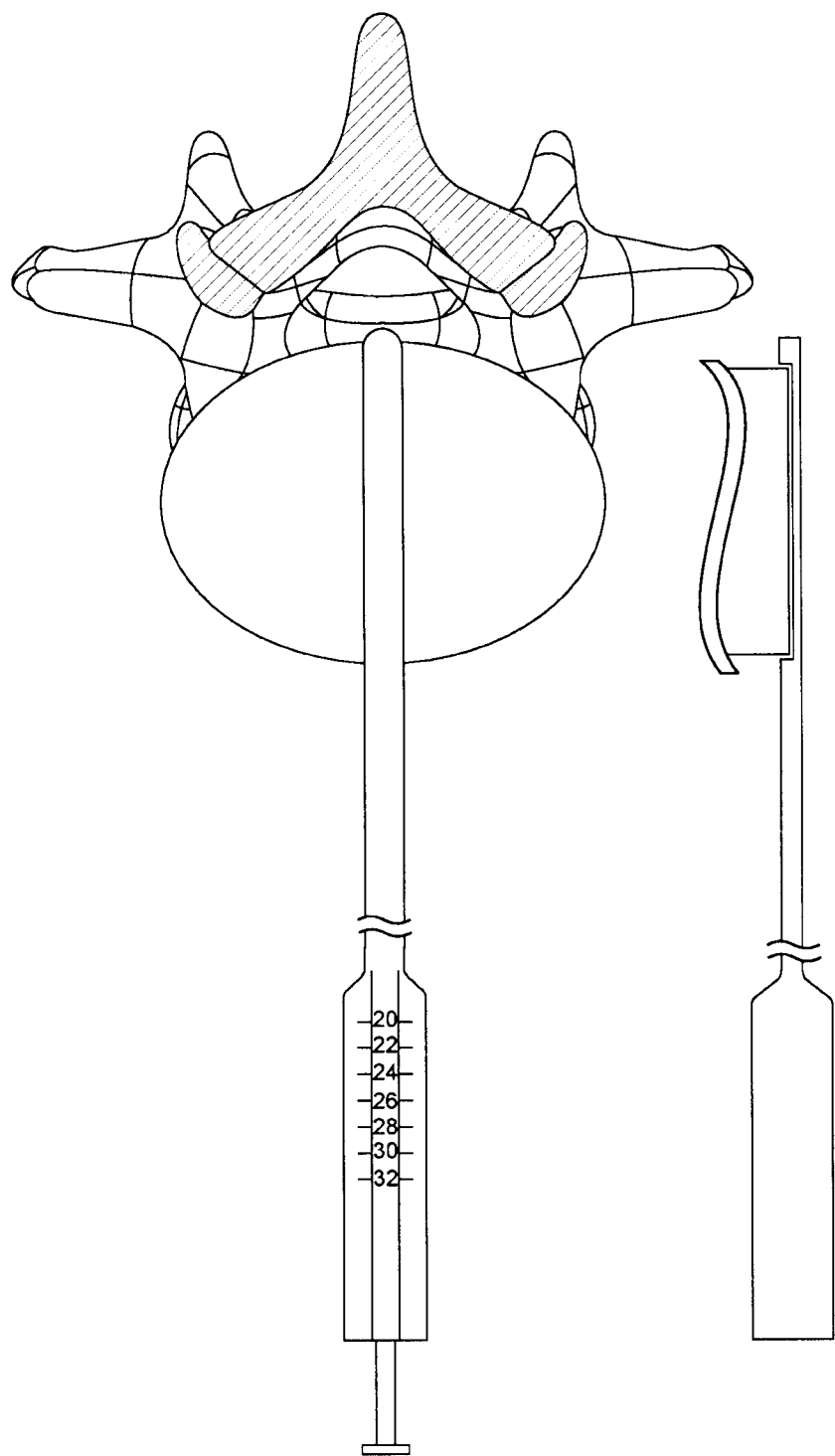
FIG. 19 is a schematic diagram illustrating one step in the placement of the anterior cage of the three column spinal fixation implant of the present invention.
Figure 20:
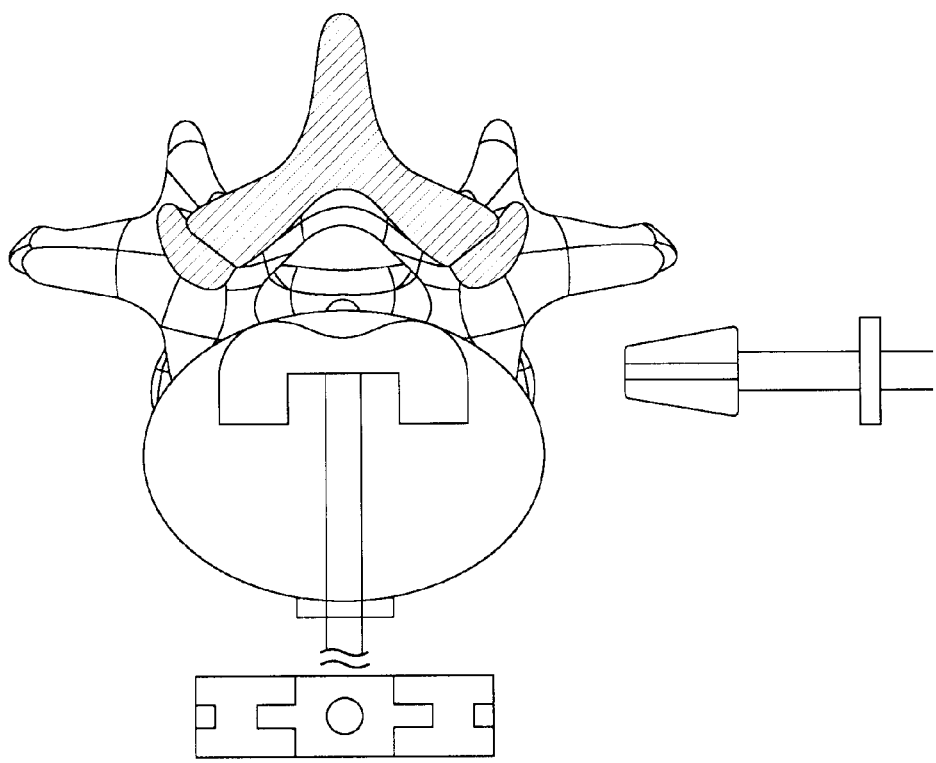
FIG. 20 is a schematic diagram illustrating another step in the placement of the anterior cage of the three column spinal fixation implant of the present invention.
Figure 21:
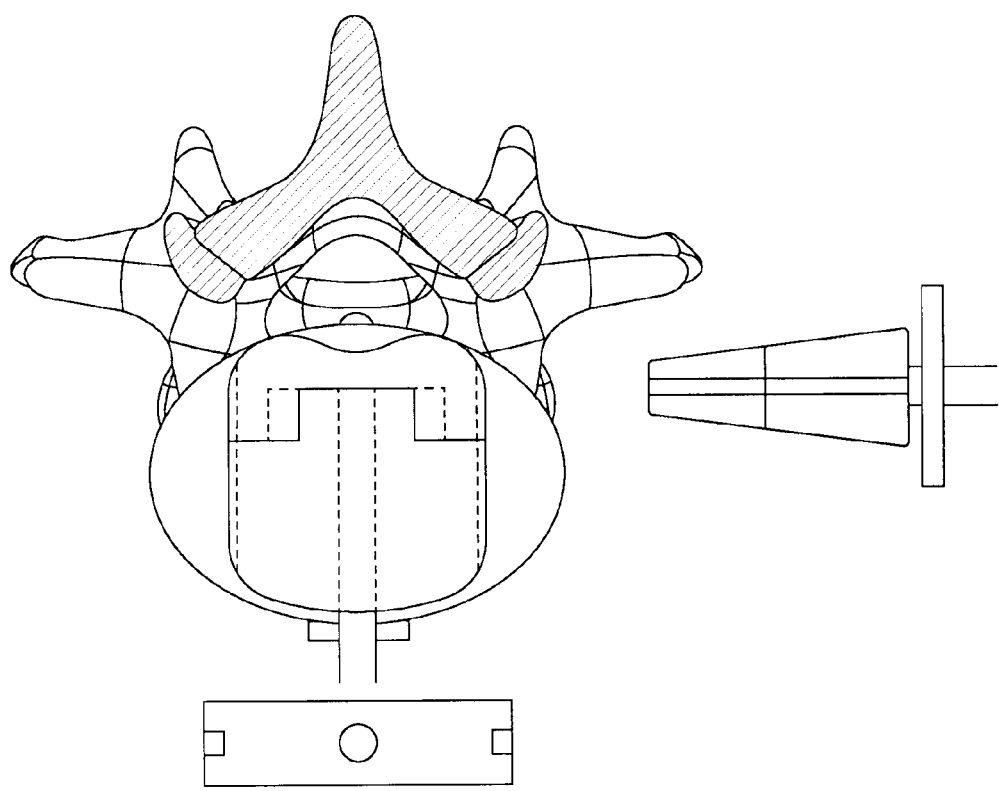
FIG. 21 is a schematic diagram illustrating a further step in the placement of the anterior cage of the three column spinal fixation implant of the present invention.
Figure 22:
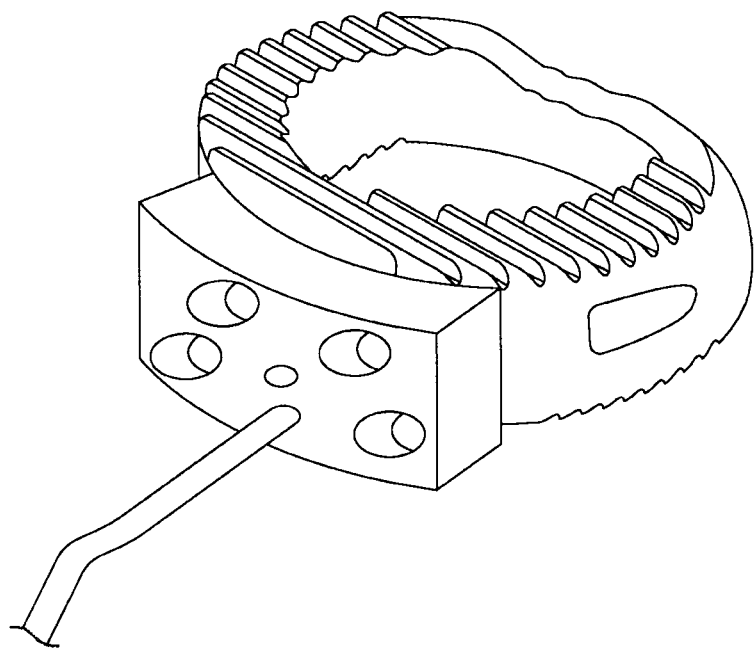
FIG. 22 is a schematic diagram illustrating a still further step in the placement of the anterior cage of the three column spinal fixation implant of the present invention.
Figure 23:
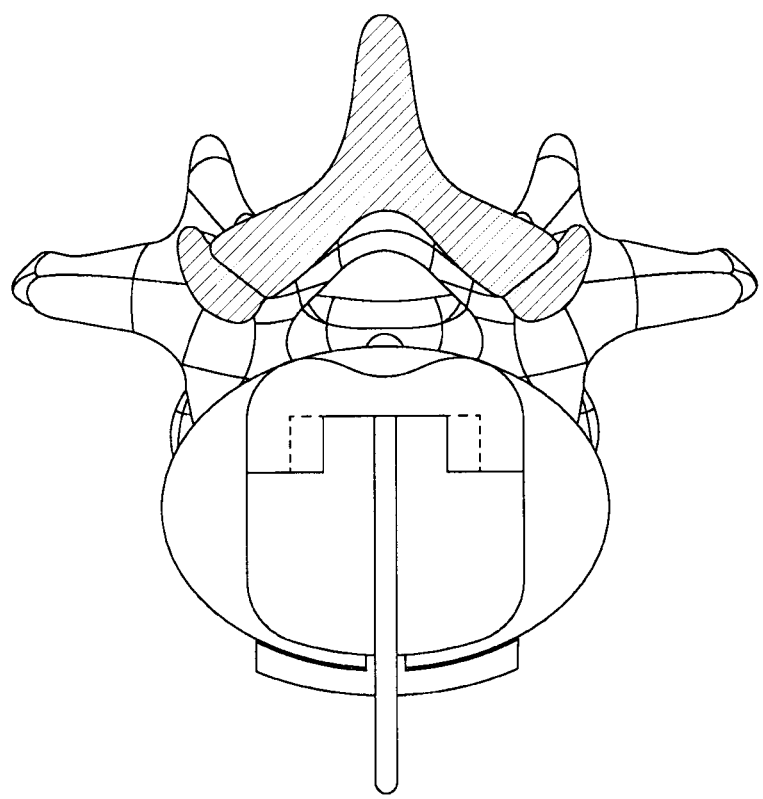
FIG. 23 is a schematic diagram illustrating a still further step in the placement of the anterior cage of the three column spinal fixation implant of the present invention.

Referring now specifically to FIGS. 19-24, in various exemplary embodiments, the surgical procedure of the present invention begins with the removal of the anterior disc and the insertion of a pre-machined trial implant that closely matches the required disc height, after measurement of the depth of the disc space (see FIG. 19). Ultimately, the cage is then inserted and a drill guide is coupled to the cage (see FIG. 22), with holes for the fixation screws drilled into the vertebral body endplates. The disc is removed in a typical fashion, using rongeurs, pituitaries, curettes, and similar instrumentation, well known to those of ordinary skill in the art. Once the disc is removed, a series of (optionally interlocking multi-piece) paddle distractors are used (see FIGS. 20 and 21). The paddle distractors are placed in the disc space with the flat sides adjacent to the vertebral endplates, for example, and are then rotated ninety degrees. This rotation widens the disc space and distracts the vertebral bodies apart. Alternatively, the height at the front and rear of the disc space is measured using separate interlocking paddle pieces.

Figure 24:
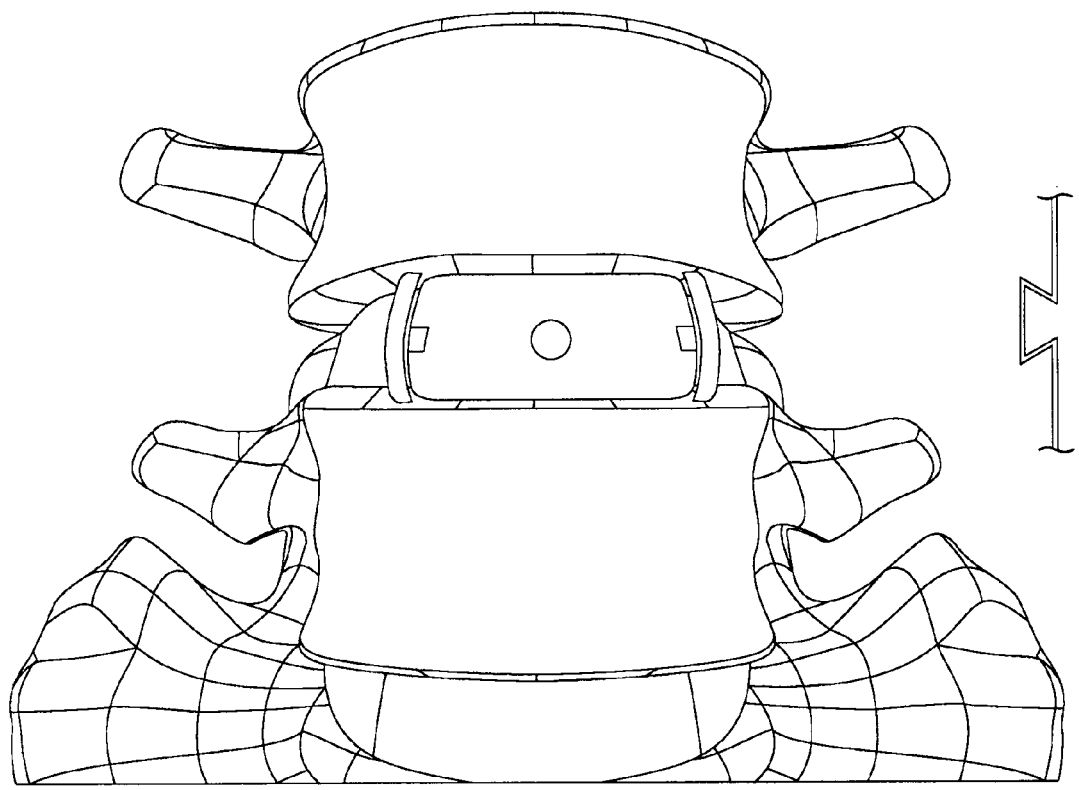
FIG. 24 is a schematic diagram illustrating a still further step in the placement of the anterior cage of the three column spinal fixation implant of the present invention.

Once the disc has been cleared out and the posterior longitudinal ligament has been removed, spanners are optionally inserted on either side of the disc space, acting as guide structures for subsequent insertions (see FIG. 24). These spanners each have a groove running along their lengths from front to back. Various gage blocks of different heights are designed to slide down the spanner grooves. The surgeon selects a certain gage block and slides it down the guides to the posterior portion of the vertebrae and then takes a lateral x-ray to determine if the gage block has created the required height. If enough distraction is not created, the surgeon chooses a taller gage block, etc. Once the posterior portion of the disc space has been properly measured, the anterior portion of the disc space can be gaged and measured in a similar fashion. Once the disc space height requirements have been determined, an appropriately sized drill guide targeting jig can be inserted. The targeting jig is also slid down onto the guides located on the staples. Using x-rays, fluoroscopy, image guidance, or the like, the angulation of the drill holes is determined. Using x-ray markers, an image of the pedicle and the anterior drill is taken. The x-ray should be positioned such that the x-ray pin lines up precisely with the posterior pedicle. The x-ray pin can be rotated in the jig so that the exact trajectory can be determined. Multiple x-rays may need to be taken. Once the drill guide is correctly positioned, it is locked into position (see FIG. 22). This can be done by either screwing the drilling guide to the cage or by some other method. Optionally, a pin is inserted into the drill guide and advanced through the vertebral body and pushed through the posterior pedicle. The pin is left in place temporarily. The same procedure is performed for the remaining drill guides. Once all the pins have been inserted, an anterior-posterior and lateral x-rays can be taken to confirm placement. The pins and jig are then removed, with the staples left in place. The appropriate sized implant is chosen from the initial measurements. The implant is placed on an inserter and placed into the disc space by aligning the two keels on the implant with the grooves on the staples. Once the implant has been inserted to the correct depth based on limits on the staple grooves, the inserter instrument is removed. The screws are then placed through the holes created by the guide pins and/or drilling. Once all of the screws are inserted, they are locked in position and the patient wound is closed. The patient is then flipped 180 degrees face down and exposure is made at the affected levels that were worked anteriorly. The spinous processes are exposed, a tensiometer is applied, and a decision is made to posteriorly apply an interspinous tension band or include tulips on the pedicle screws. If a decision is made to apply tulips to the pedicle screws, the pedicles are exposed and the existing screws are found. If necessary, a reamer may be used to remove bone. The heads are connected to the screws and locked in position. The rods or other connectors are connected to the superior and inferior heads. The affected level may be compressed using a compressor to get the correct spinal alignment. X-rays are taken to confirm the final alignment. If the tensiometer indicates sufficient stiffness, then the pedicles screws can be broken off percutaneously, if necessary, and the site closed.

Figure 25:
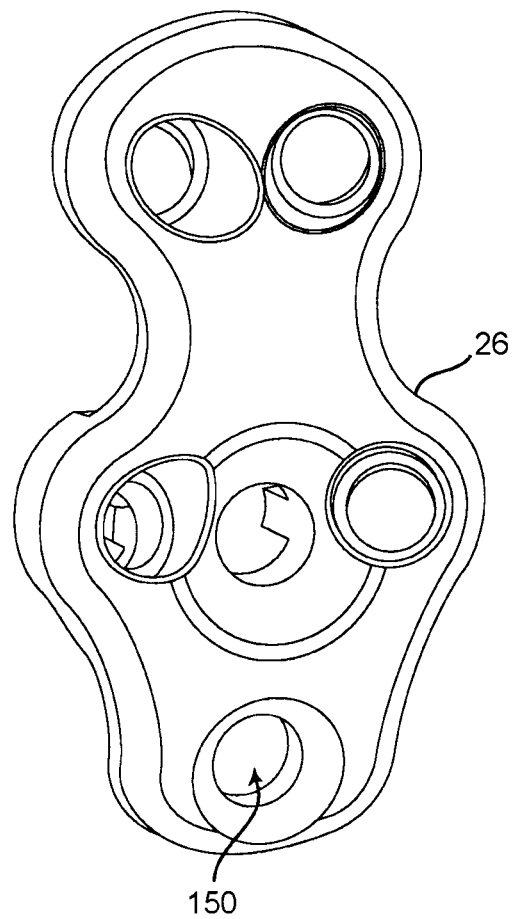
FIG. 25 is a perspective view of one exemplary embodiment of the anterior plate of the present invention including an additional screw hole for receiving a lag screw for segmental reduction, the lag screw disposed substantially parallel to one of the vertebral endplates of the spine of the patient (in this case the lower vertebral endplate opposite the other screws utilized)

FIG. 25 is a perspective view of one exemplary embodiment of the anterior plate 26 of the present invention including an additional screw hole 150 for receiving a lag screw 152 (FIG. 26) for segmental reduction, the lag screw 152 disposed substantially parallel to one of the vertebral endplates of the spine of the patient (in this case the lower vertebral endplate opposite the other screws utilized).

Figure 26:
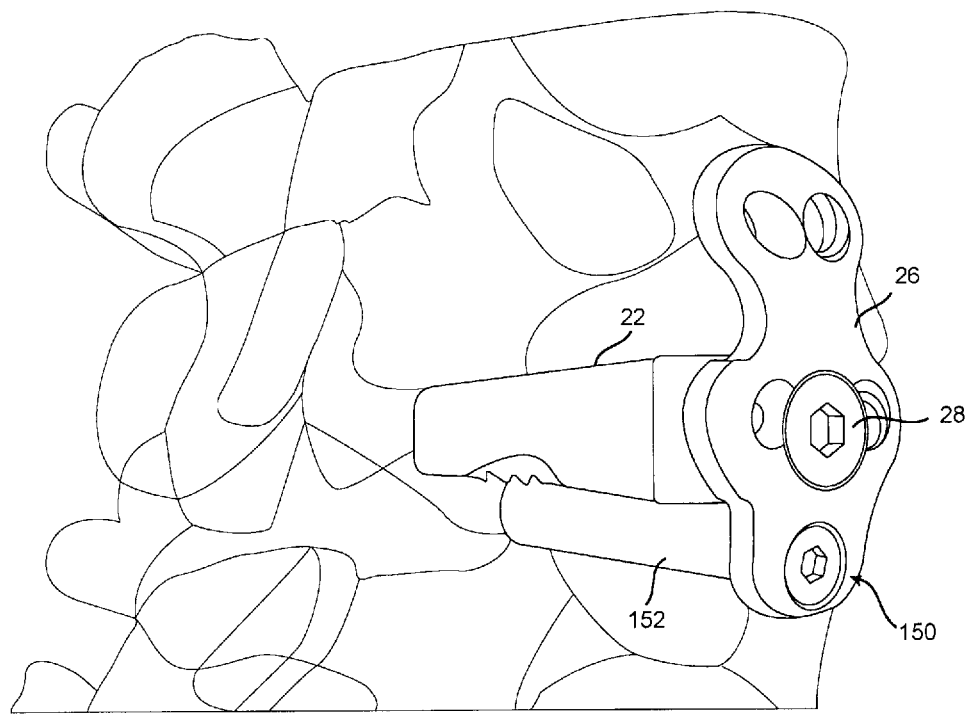
FIG. 26 is another perspective view of one exemplary embodiment of the anterior plate of the present invention including an additional screw hole for receiving a lag screw for segmental reduction, the lag screw disposed substantially parallel to one of the vertebral endplates of the spine of the patient (in this case the lower vertebral endplate opposite the other screws utilized).

FIG. 26 is another perspective view of one exemplary embodiment of the anterior plate 26 of the present invention including the additional screw hole 150 for receiving the lag screw 152 for segmental reduction, the lag screw 152 disposed substantially parallel to one of the vertebral endplates of the spine of the patient (in this case the lower vertebral endplate opposite the other screws utilized).

Although the present invention is illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following non-limiting claims.

What is claimed is:

1. A three column spinal fixation implant, comprising:
an anterior cage configured to be disposed in an intervertebral space between adjacent vertebral bodies in a spine of a patient;
one or more anterior screws coupled to the anterior cage and configured to extend posteriorly from the anterior cage through a portion of one or more of the adjacent vertebral bodies and into or through posterior bony structures of the spine of the patient;
one or more posterior headbodies coupled to the one or more anterior screws opposite the anterior cage; and
one or more connecting structures coupled to the one or more posterior headbodies; wherein the one or more posterior headbodies are coupled to the one or more anterior screws via one or more posterior screws that threadingly engage the one or more anterior screws in a coaxial alignment or via one or more compression fittings that compressively engage the one or more anterior screws in a coaxial alignment; and
wherein the three column spinal fixation implant configured to provide structural stability to the spine of the patient across a first anterior column, a second middle column, and a third posterior column thereof.

2. The implant of claim 1, further comprising an anterior plate coupled to the anterior cage.

3. The implant of claim 2, wherein the one or more anterior screws are coupled to the anterior cage through the anterior plate.

4. The implant of claim 3, wherein the one or more anterior screws comprise a pair of anterior screws that are coupled to both the anterior cage and the anterior plate and a pair of anterior screws that are coupled only to the anterior plate.

5. The implant of claim 1, wherein the anterior cage comprises one or more friction surfaces configured to hold the anterior cage in the intervertebral space.

6. The implant of claim 1, wherein the anterior cage defines one or more internal voids configured to contain a bone graft material.

7. The implant of claim 1, wherein the anterior cage is manufactured from one or more of a surgically implantable polymeric material and a surgically implantable metallic material.

8. The implant of claim 1, wherein the one or more connecting structures comprise one or more connecting rods that are coupled to adjacent posterior headbodies.

9. The implant of claim 1, wherein the one or more connecting structures are coupled to adjacent posterior headbodies through a space between adjacent spinous processes of the spine of the patient, thereby configured to distract the adjacent spinous processes.

10. The implant of claim 1, wherein the one or more connecting structures are coupled to adjacent posterior headbodies parallel to adjacent spinous processes of the spine of the patient, thereby configured to distract the adjacent spinous processes.

11. The implant of claim 1, wherein the one or more connecting structures couple the one or more headbodies to one or more facets of the spine of the patient.

12. A three column spinal fixation implant, comprising:
an anterior cage configured to be disposed in an intervertebral space between adjacent vertebral bodies in a spine of a patient;
an anterior plate coupled to the anterior cage;
a pair of anterior screws coupled to the anterior cage and the anterior plate and extending posteriorly from the anterior cage and the anterior plate through a portion of one or more of the adjacent vertebral bodies and into or through posterior bony structures of the spine of the patient;
a pair of anterior screws coupled to the anterior plate and extending posteriorly from the anterior plate through a portion of one or more of the adjacent vertebral bodies and into or through posterior bony structures of the spine of the patient;
a plurality of posterior headbodies coupled to the anterior screws opposite the anterior cage and the anterior plate; and
one or more connecting structures coupled to the plurality of posterior headbodies; wherein the one or more posterior headbodies are coupled to the one or more anterior screws via one or more posterior screws that threadingly engage the one or more anterior screws in a coaxial alignment or via one or more compression fittings that compressively engage the one or more anterior screws in a coaxial alignment; and
wherein the three column spinal fixation implant provides structural stability to the spine of the patient across a first anterior column, a second middle column, and a third posterior column thereof.

* * * * *